(12) United States Patent
Kim

(10) Patent No.: US 11,554,499 B2
(45) Date of Patent: Jan. 17, 2023

(54) ROBOT AND METHOD FOR CONTROLLING THE SAME

(71) Applicant: LG ELECTRONICS INC., Seoul (KR)

(72) Inventor: Namgeon Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 410 days.

(21) Appl. No.: 16/744,587

(22) Filed: Jan. 16, 2020

(65) Prior Publication Data
US 2021/0138661 A1 May 13, 2021

(30) Foreign Application Priority Data

Nov. 11, 2019 (KR) ........................ 10-2019-0143261

(51) Int. Cl.
| | | |
|---|---|---|
| *G10L 15/08* | (2006.01) | |
| *B25J 13/00* | (2006.01) | |
| *B25J 11/00* | (2006.01) | |
| *B25J 19/02* | (2006.01) | |

(52) U.S. Cl.
CPC ......... *B25J 13/003* (2013.01); *B25J 11/0015* (2013.01); *B25J 19/023* (2013.01); *G10L 15/08* (2013.01); *G10L 2015/088* (2013.01)

(58) Field of Classification Search
CPC .... B25J 13/003; B25J 11/0015; B25J 19/023; B25J 11/0005; B25J 9/161; B25J 9/1674; B25J 9/1697; B25J 19/061; G10L 15/08; G10L 2015/088; G10L 25/51; A61B 5/0022; A61B 5/7282; A61B 5/1116; A61B 5/1128; A61B 5/1176; A61B 5/0077; A61B 5/7267; A61B 5/1172; A61B 5/4809; A61B 5/4812; A61B 5/7405; A61B 2503/04; A61B 2560/0242; A61B 2562/0204; A61B 2562/0219; A61B 2562/0223; A61B 2562/0257; A61B 5/4806; G08B 21/0208
See application file for complete search history.

(56) References Cited

U.S. PATENT DOCUMENTS

| | | | | |
|---|---|---|---|---|
| 2012/0315016 | A1* | 12/2012 | Fung ..................... | H04N 5/2252 348/222.1 |
| 2018/0376111 | A1* | 12/2018 | Mrowiec ................. | G10L 25/72 |
| 2021/0158837 | A1* | 5/2021 | Saki ....................... | G06N 3/0454 |

FOREIGN PATENT DOCUMENTS

| | | | | |
|---|---|---|---|---|
| CN | 108604401 A | * | 9/2018 | ....... G08B 13/19619 |
| CN | 210181743 U | * | 3/2020 | |

* cited by examiner

*Primary Examiner* — Abul K Azad
(74) *Attorney, Agent, or Firm* — Ked & Associates, LLP

(57) ABSTRACT

A robot according to the present disclosure comprises: a microphone; a camera disposed to face a predetermined direction; and a processor configured to: inactivate driving of the camera and activate driving of the microphone, if a driving mode of the robot is set to a user monitoring mode; acquire a sound signal through the microphone; activate the driving of the camera based on an event estimated from the acquired sound signal; confirm the event from the image acquired through the camera; and control at least one constituent included in the robot to perform an operation based on the confirmed event.

20 Claims, 10 Drawing Sheets

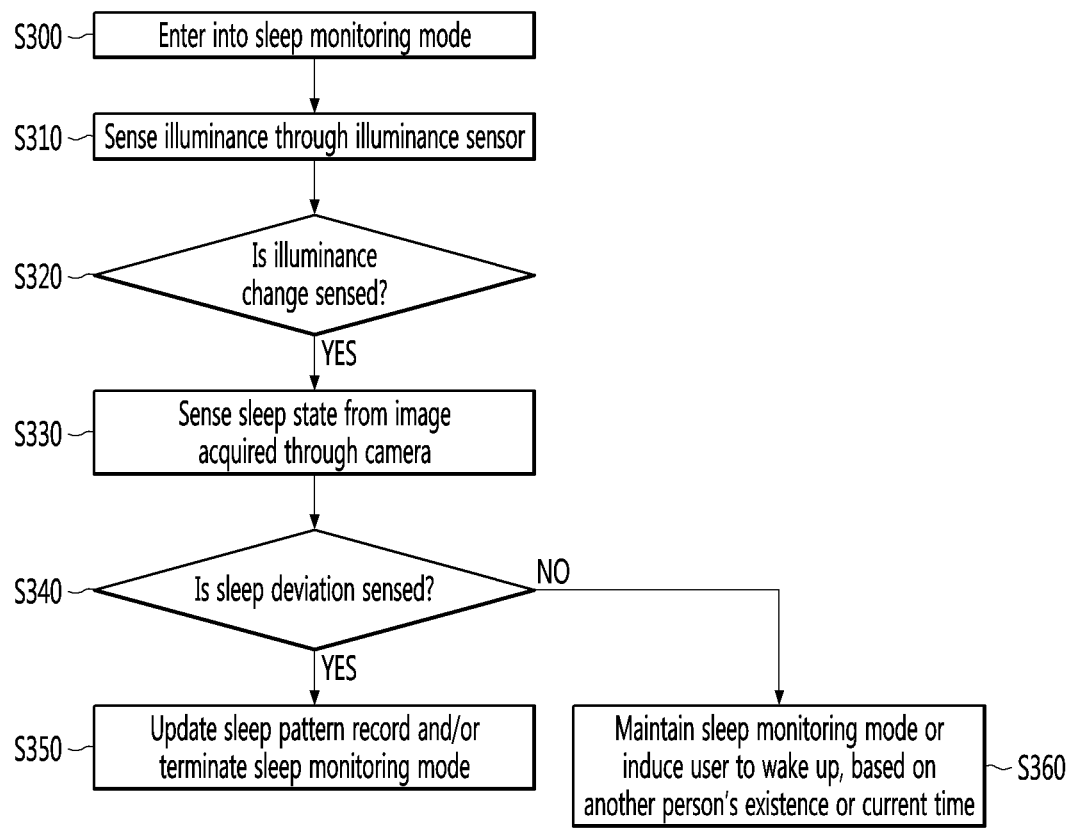

# ROBOT AND METHOD FOR CONTROLLING THE SAME

CROSS-REFERENCE TO RELATED APPLICATIONS

The present application claims priority under 35 U.S.C. 119 and 35 U.S.C. 365 to Korean Patent Application No. 10-2019-0143261 (filed on Nov. 11, 2019), which is hereby incorporated by reference in its entirety.

BACKGROUND

The present disclosure relates to a robot and a method for controlling the robot.

A robot may refer to a machine that automatically processes or operates a given task by its own ability, and application fields of the robots may be generally classified into a variety of fields such as industrial robots, medical robots, space robots, military robots, and the like. In recent, communication robots that can perform communication or interaction with humans through a voice, a gesture or the like are on a constant rise.

Such communication robots may include various kinds of robots such as a guide robot that is disposed in a specific position and guides all kinds of information to a user, a home robot provided at home, and the like. In addition, the communication robots may include an educational robot that guides or assists learning of a learner through the interaction with the learner.

Communication robots may be implemented to perform the interaction with the user, the learner or the like, by using a variety of constituents. For example, the communication robot may include a microphone for acquiring a sound created around the robot, or a camera for acquiring an image around the robot.

Such a robot may operate in response to an utterance of the user's wakeup word, and the like, sense a change of a surrounding environment using various sensors, and automatically perform a predetermined operation based on a sensed result.

However, when the robot operates by sensing the change of the surrounding environment in an unnecessary situation, waste of resources may be caused, electricity consumption is unnecessarily increased, and the user's inconvenience or trouble may be caused.

SUMMARY

One technical problem to be solved by the present disclosure is intended to provide a robot that can minimize an interrupt for a user in situations such the user's sleep and the like.

The other technical problem to be solved by the present disclosure is intended to provide a robot that can effectively monitor the user's state or a surrounding situation, while minimizing power consumption.

A robot according to an embodiment of the present disclosure may inactivate driving of the camera and activate driving of the microphone, if a driving mode of the robot is set to a user monitoring mode; activate the driving of the camera based on an event estimated from the sound signal acquired through the microphone; and perform an operation based on the event confirmed from the image acquired through the activated camera.

According to an embodiment, the robot may activate the driving of the camera, if the estimated event is set to a notification event.

According to an embodiment, if the event confirmed from the acquired image is set to the notification event, the robot may output a notification associated with the confirmed event, or transmit the notification to a mobile terminal.

According to an embodiment, the robot may update a history associated with a current state of the user based on the event confirmed from the acquired image.

According to an embodiment, the user monitoring mode may include a sleep history mode driven when the user is asleep, and if the user is sensed not to be asleep, the robot may update the sleep history with the user waking up at a time of creating the sound signal or at a time of acquiring the image, and terminate the sleep monitoring mode.

According to an embodiment, if the user is sensed to be asleep, the robot may update the sleep history based on whether to make a movement of the user, or based on kinds of sounds created from the user.

According to an embodiment, when entering into the user monitoring mode, the robot may control the at least one motor such that the camera faces a position including the user.

BRIEF DESCRIPTION OF THE DRAWINGS

FIG. 10 is a flowchart for explaining an embodiment for a control operation of the robot entering into the sleep monitoring mode.

DETAILED DESCRIPTION

Figure 1:
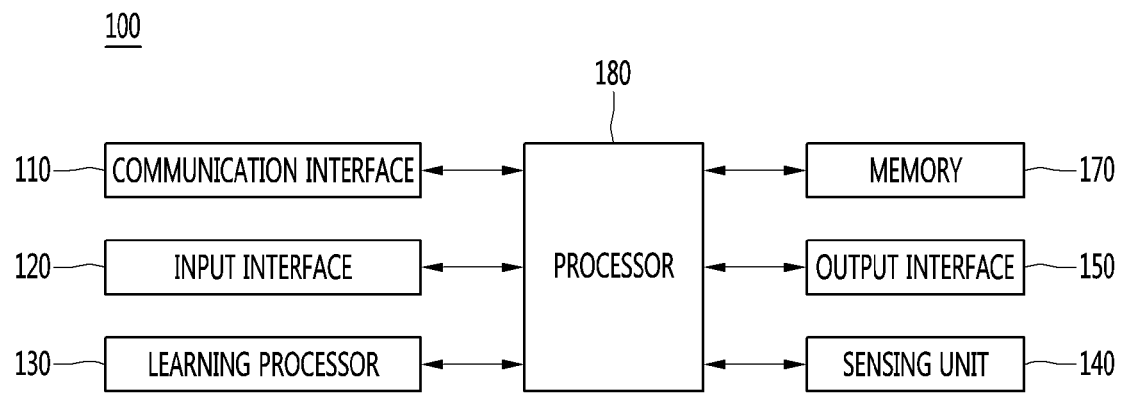
FIG. 1 illustrates an AI device 100 including a robot according to an embodiment of the present disclosure.

Description will now be given in detail according to exemplary embodiments disclosed herein, with reference to the accompanying drawings. The accompanying drawings are used to help easily understand the embodiments disclosed in this specification and it should be understood that the embodiments presented herein are not limited by the accompanying drawings. As such, the present disclosure should be construed to extend to any alterations, equivalents and substitutes in addition to those which are particularly set out in the accompanying drawings.

A robot may refer to a machine that automatically processes or operates a given task by its own ability. In particular, a robot having a function of recognizing an environment and performing a self-determination operation may be referred to as an intelligent robot.

Robots may be classified into industrial robots, medical robots, home robots, military robots, and the like according to the use purpose or field.

The robot includes a driving unit may include an actuator or a motor and may perform various physical operations such as moving a robot joint. In addition, a movable robot may include a wheel, a brake, a propeller, and the like in a driving unit, and may travel on the ground through the driving unit or fly in the air.

Artificial intelligence refers to the field of studying artificial intelligence or methodology for making artificial intelligence, and machine learning refers to the field of defining various issues dealt with in the field of artificial intelligence and studying methodology for solving the various issues. Machine learning is defined as an algorithm that enhances the performance of a certain task through a steady experience with the certain task.

An artificial neural network (ANN) is a model used in machine learning and may mean a whole model of problem-solving ability which is composed of artificial neurons (nodes) that form a network by synaptic connections. The artificial neural network can be defined by a connection pattern between neurons in different layers, a learning process for updating model parameters, and an activation function for generating an output value.

The artificial neural network may include an input layer, an output layer, and optionally one or more hidden layers. Each layer includes one or more neurons, and the artificial neural network may include a synapse that links neurons to neurons. In the artificial neural network, each neuron may output the function value of the activation function for input signals, weights, and deflections input through the synapse.

Model parameters refer to parameters determined through learning and include a weight value of synaptic connection and deflection of neurons. A hyperparameter means a parameter to be set in the machine learning algorithm before learning, and includes a learning rate, a repetition number, a mini batch size, and an initialization function.

The purpose of the learning of the artificial neural network may be to determine the model parameters that minimize a loss function. The loss function may be used as an index to determine optimal model parameters in the learning process of the artificial neural network.

Machine learning may be classified into supervised learning, unsupervised learning, and reinforcement learning according to a learning method.

The supervised learning may refer to a method of learning an artificial neural network in a state in which a label for learning data is given, and the label may mean the correct answer (or result value) that the artificial neural network must infer when the learning data is input to the artificial neural network. The unsupervised learning may refer to a method of learning an artificial neural network in a state in which a label for learning data is not given. The reinforcement learning may refer to a learning method in which an agent defined in a certain environment learns to select a behavior or a behavior sequence that maximizes cumulative compensation in each state.

Machine learning, which is implemented as a deep neural network (DNN) including a plurality of hidden layers among artificial neural networks, is also referred to as deep learning, and the deep learning is part of machine learning. In the following, machine learning is used to mean deep learning.

FIG. FIG. 1 illustrates an AI device 100 including a robot according to an embodiment of the present disclosure.

The AI device 100 may be implemented by a stationary device or a mobile device, such as a TV, a projector, a mobile phone, a smartphone, a desktop computer, a notebook, a digital broadcasting terminal, a personal digital assistant (PDA), a portable multimedia player (PMP), a navigation device, a tablet PC, a wearable device, a set-top box (STB), a DMB receiver, a radio, a washing machine, a refrigerator, a desktop computer, a digital signage, a robot, a vehicle, and the like.

Referring to FIG. 1, the AI device 100 may include a communication interface 110, an input interface 120, a learning processor 130, a sensing unit 140, an output interface 150, a memory 170, and a processor 180.

The communication interface 110 may transmit and receive data to and from external devices such as other AI devices 100a to 100e and the AI server 200 by using wire/wireless communication technology. For example, the communication interface 110 may transmit and receive sensor information, a user input, a learning model, and a control signal to and from external devices.

At this time, the communication technology used by the communication interface 110 includes GSM (Global System for Mobile communication), CDMA (Code Division Multi Access), LTE (Long Term Evolution), 5G, WLAN (Wireless LAN), Wi-Fi (Wireless-Fidelity), Bluetooth™, RFID (Radio Frequency Identification), Infrared Data Association (IrDA), ZigBee, NFC (Near Field Communication), and the like.

The input interface 120 may acquire various kinds of data.

At this time, the input interface 120 may include a camera for inputting a video signal, a microphone for receiving an audio signal, and a user input interface for receiving information from a user. The camera or the microphone may be treated as a sensor, and the signal acquired from the camera or the microphone may be referred to as sensing data or sensor information.

The input interface 120 may acquire a learning data for model learning and an input data to be used when an output is acquired by using learning model. The input interface 120 may acquire raw input data. In this case, the processor 180 or the learning processor 130 may extract an input feature by preprocessing the input data.

The learning processor 130 may learn a model composed of an artificial neural network by using learning data. The learned artificial neural network may be referred to as a learning model. The learning model may be used to an infer result value for new input data rather than learning data, and the inferred value may be used as a basis for determination to perform a certain operation.

At this time, the learning processor 130 may perform AI processing together with the learning processor 240 of the AI server 200.

At this time, the learning processor 130 may include a memory integrated or implemented in the AI device 100. Alternatively, the learning processor 130 may be implemented by using the memory 170, an external memory directly connected to the AI device 100, or a memory held in an external device.

The sensing unit 140 may acquire at least one of internal information about the AI device 100, ambient environment information about the AI device 100, and user information by using various sensors.

At this time, examples of the sensors included in the sensing unit 140 may include a proximity sensor, an illuminance sensor, an acceleration sensor, a magnetic sensor, a gyro sensor, an inertial sensor, an RGB sensor, an IR sensor, a fingerprint recognition sensor, an ultrasonic sensor, an optical sensor, a microphone, a lidar, and a radar.

The output interface 150 may generate an output related to a visual sense, an auditory sense, or a haptic sense.

At this time, the output interface 150 may include a display for outputting time information, a speaker for outputting auditory information, and a haptic module for outputting haptic information.

The memory 170 may store data that supports various functions of the AI device 100. For example, the memory 170 may store input data acquired by the input interface 120, learning data, a learning model, a learning history, and the like.

The processor 180 may determine at least one executable operation of the AI device 100 based on information determined or generated by using a data analysis algorithm or a machine learning algorithm. The processor 180 may control the components of the AI device 100 to execute the determined operation.

To this end, the processor 180 may request, search, receive, or utilize data of the learning processor 130 or the memory 170. The processor 180 may control the components of the AI device 100 to execute the predicted operation or the operation determined to be desirable among the at least one executable operation.

At this, time, when the connection of an external device is required to perform the determined operation, the processor 180 may generate a control signal for controlling the external device and may transmit the generated control signal to the external device.

The processor 180 may acquire intention information for the user input and may determine the user's requirements based on the acquired intention information.

At this time, the processor 180 may acquire the intention information corresponding to the user input by using at least one of a speech to text (STT) engine for converting speech input into a text string or a natural language processing (NLP) engine for acquiring intention information of a natural language.

At this time, at least one of the STT engine or the NLP engine may be configured as an artificial neural network, at least part of which is learned according to the machine learning algorithm. At least one of the STT engine or the NLP engine may be learned by the learning processor 130, may be learned by the learning processor 240 of the AI server 200, or may be learned by their distributed processing.

The processor 180 may collect history information including the operation contents of the AI apparatus 100 or the user's feedback on the operation and may store the collected history information in the memory 170 or the learning processor 130 or transmit the collected history information to the external device such as the AI server 200. The collected history information may be used to update the learning model.

The processor 180 may control at least part of the components of AI device 100 so as to drive an application program stored in memory 170. Furthermore, the processor 180 may operate two or more of the components included in the AI device 100 in combination so as to drive the application program.

Figure 2:
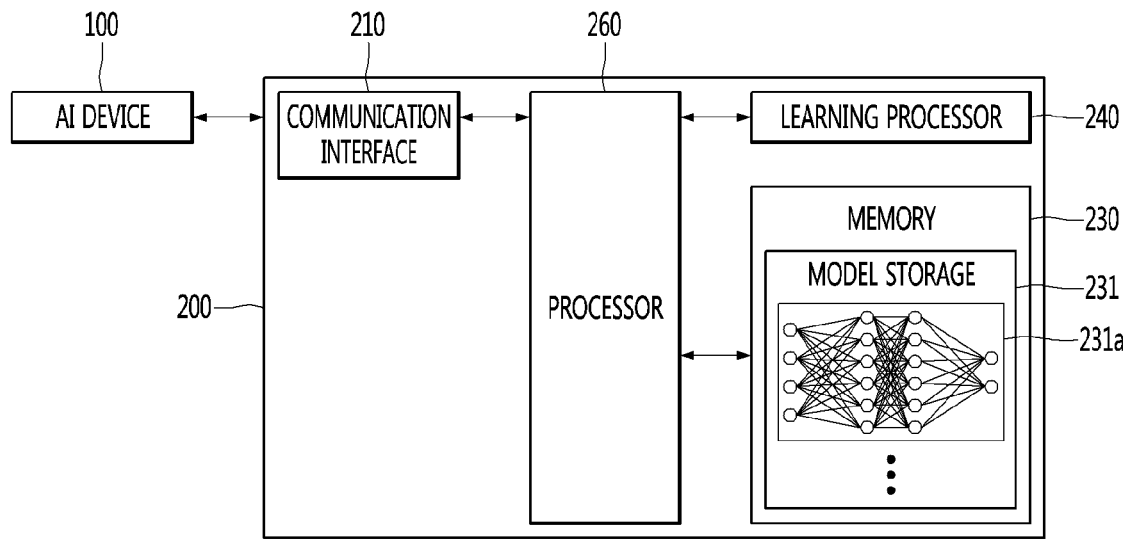
FIG. 2 illustrates an AI server 200 connected to a robot according to an embodiment of the present disclosure.

FIG. FIG. 2 illustrates an AI server 200 connected to a robot according to an embodiment of the present disclosure.

Referring to FIG. 2, the AI server 200 may refer to a device that learns an artificial neural network by using a machine learning algorithm or uses a learned artificial neural network. The AI server 200 may include a plurality of servers to perform distributed processing, or may be defined as a 5G network. At this time, the AI server 200 may be included as a partial configuration of the AI device 100, and may perform at least part of the AI processing together.

The AI server 200 may include a communication interface 210, a memory 230, a learning processor 240, a processor 260, and the like.

The communication interface 210 can transmit and receive data to and from an external device such as the AI device 100.

The memory 230 may include a model storage 231. The model storage 231 may store a learning or learned model (or an artificial neural network 231a) through the learning processor 240.

The learning processor 240 may learn the artificial neural network 231a by using the learning data. The learning model may be used in a state of being mounted on the AI server 200 of the artificial neural network, or may be used in a state of being mounted on an external device such as the AI device 100.

The learning model may be implemented in hardware, software, or a combination of hardware and software. If all or part of the learning models are implemented in software, one or more instructions that constitute the learning model may be stored in memory 230.

The processor 260 may infer the result value for new input data by using the learning model and may generate a response or a control command based on the inferred result value.

Figure 3:
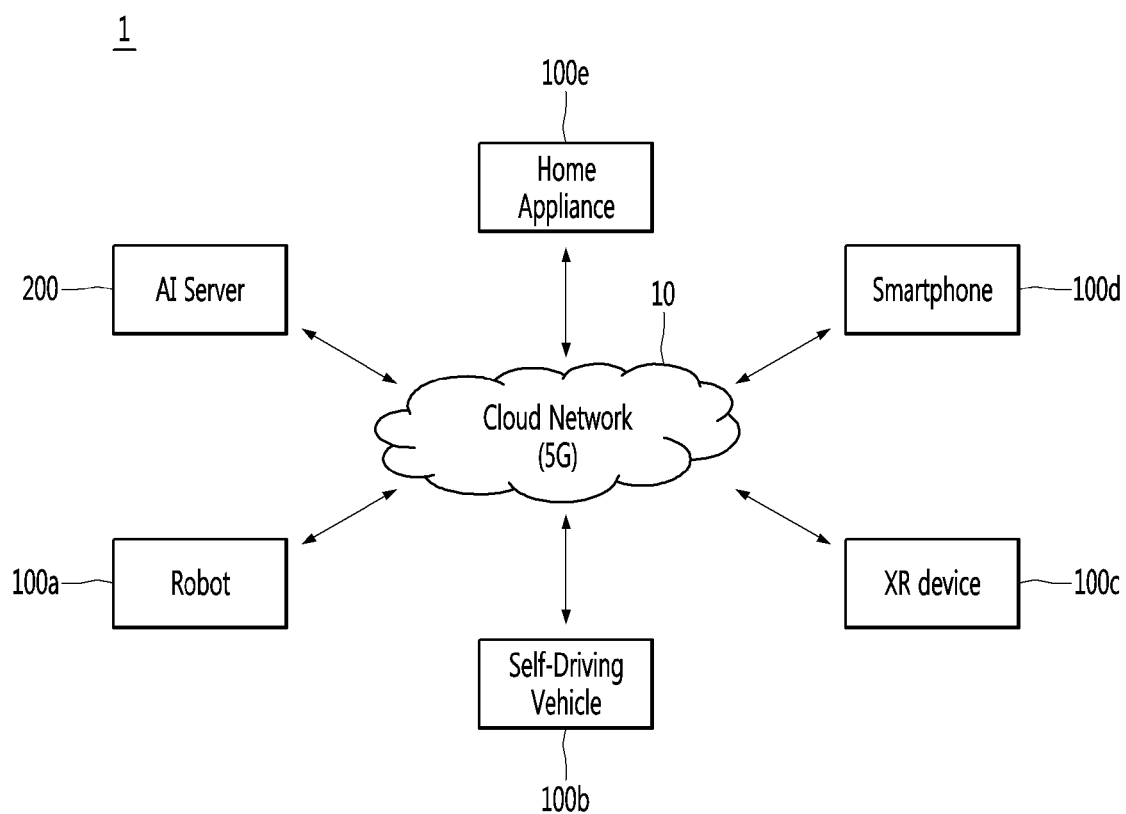
FIG. 3 illustrates an AI system 1 according to an embodiment of the present disclosure.

FIG. 3 illustrates an AI system 1 according to an embodiment of the present disclosure.

Referring to FIG. 3, in the AI system 1, at least one of an AI server 200, a robot 100a, a self-driving vehicle 100b, an XR device 100c, a smartphone 100d, or a home appliance 100e is connected to a cloud network 10. The robot 100a, the self-driving vehicle 100b, the XR device 100c, the smartphone 100d, or the home appliance 100e, to which the AI technology is applied, may be referred to as AI devices 100a to 100e.

The cloud network 10 may refer to a network that forms part of a cloud computing infrastructure or exists in a cloud computing infrastructure. The cloud network 10 may be configured by using a 3G network, a 4G or LTE network, or a 5G network.

That is, the devices 100a to 100e and 200 configuring the AI system 1 may be connected to each other through the cloud network 10. In particular, each of the devices 100a to 100e and 200 may communicate with each other through a base station, but may directly communicate with each other without using a base station.

The AI server 200 may include a server that performs AI processing and a server that performs operations on big data.

The AI server 200 may be connected to at least one of the AI devices constituting the AI system 1, that is, the robot 100a, the self-driving vehicle 100b, the XR device 100c, the smartphone 100d, or the home appliance 100e through the cloud network 10, and may assist at least part of AI processing of the connected AI devices 100a to 100e.

At this time, the AI server 200 may learn the artificial neural network according to the machine learning algorithm instead of the AI devices 100a to 100e, and may directly store the learning model or transmit the learning model to the AI devices 100a to 100e.

At this time, the AI server 200 may receive input data from the AI devices 100a to 100e, may infer the result value for the received input data by using the learning model, may generate a response or a control command based on the inferred result value, and may transmit the response or the control command to the AI devices 100a to 100e.

Alternatively, the AI devices 100a to 100e may infer the result value for the input data by directly using the learning model, and may generate the response or the control command based on the inference result.

Hereinafter, various embodiments of the AI devices 100a to 100e to which the above-described technology is applied will be described. The AI devices 100a to 100e illustrated in FIG. 3 may be regarded as a specific embodiment of the AI device 100 illustrated in FIG. 1.

The robot 100a, to which the AI technology is applied, may be implemented as a guide robot, a carrying robot, a cleaning robot, a wearable robot, an entertainment robot, a pet robot, an unmanned flying robot, or the like.

The robot 100a may include a robot control module for controlling the operation, and the robot control module may refer to a software module or a chip implementing the software module by hardware.

The robot 100a may acquire state information about the robot 100a by using sensor information acquired from various kinds of sensors, may detect (recognize) surrounding environment and objects, may generate map data, may determine the route and the travel plan, may determine the response to user interaction, or may determine the operation.

The robot 100a may use the sensor information acquired from at least one sensor among the lidar, the radar, and the camera so as to determine the travel route and the travel plan.

The robot 100a may perform the above-described operations by using the learning model composed of at least one artificial neural network. For example, the robot 100a may recognize the surrounding environment and the objects by using the learning model, and may determine the operation by using the recognized surrounding information or object information. The learning model may be learned directly from the robot 100a or may be learned from an external device such as the AI server 200.

At this time, the robot 100a may perform the operation by generating the result by directly using the learning model, but the sensor information may be transmitted to the external device such as the AI server 200 and the generated result may be received to perform the operation.

The robot 100a may use at least one of the map data, the object information detected from the sensor information, or the object information acquired from the external apparatus to determine the travel route and the travel plan, and may control the driving unit such that the robot 100a travels along the determined travel route and travel plan.

The map data may include object identification information about various objects arranged in the space in which the robot 100a moves. For example, the map data may include object identification information about fixed objects such as walls and doors and movable objects such as pollen and desks. The object identification information may include a name, a type, a distance, and a position.

In addition, the robot 100a may perform the operation or travel by controlling the driving unit based on the control/interaction of the user. At this time, the robot 100a may acquire the intention information of the interaction due to the user's operation or speech utterance, and may determine the response based on the acquired intention information, and may perform the operation.

Figure 4:
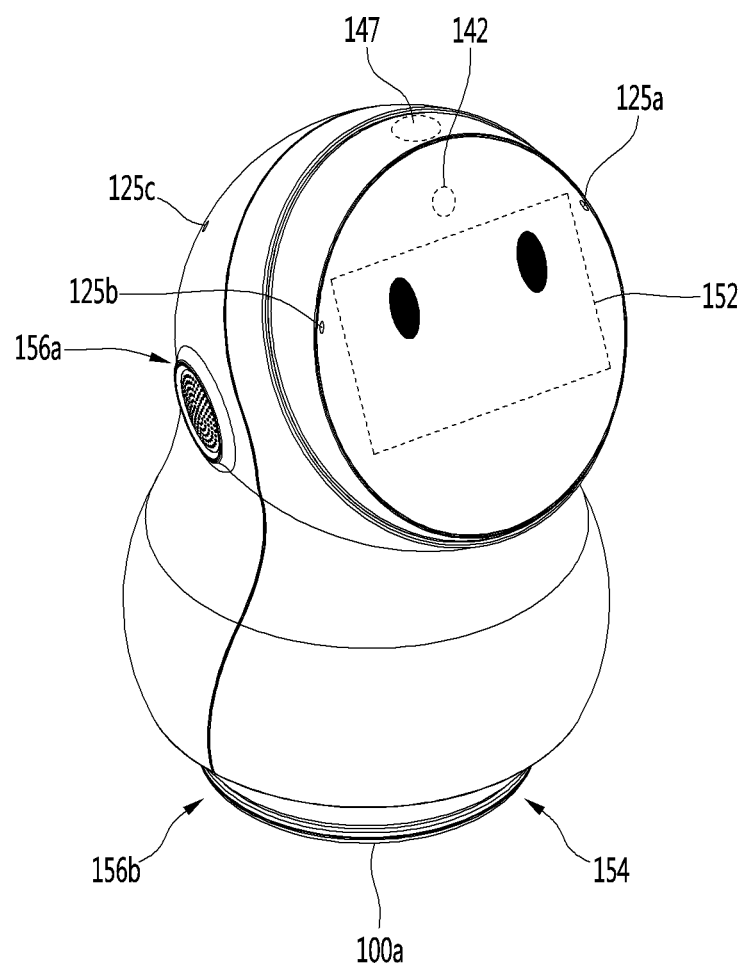
FIG. 4 is a perspective view according to an embodiment of the present disclosure.

FIG. 4 is a perspective view according to an embodiment of the present disclosure.

Referring to FIG. 4, the robot 100a may correspond to a communication robot that can provide information or a content to the user through communication or interaction with the user, or perform operations such as induction of a specific action, and the like.

For example, the robot 100a may be a home robot arranged at home. Such a home robot may provide all kinds of information or contents to the user through interaction with the user, or perform operations such as monitoring an event created at home, and the like.

In order to perform the above-described operations, the robot 100a may comprise an input and output means such as a camera 142 for acquiring an image around the user or the robot, at least one microphone 124 (see FIG. 5) for acquiring the user's voice, a sound around the robot, and the like, a touch sensor 147 for sensing a contact with a portion (e.g., a finger) of a body of the user and the like, a display 152 for outputting a graphic or a text, a speaker 154 for outputting a voice or a sound, and a light source 156 (see FIG. 5) for outputting light having a predetermined color or pattern in response to a specific event or situation.

The robot 100a may include at least one microphone hole 125a to 125c formed on an outer surface of a cover (or a case) so as to smoothly acquire an outside sound of the robot through at least one microphone 124 implemented inside. Each of the microphone holes 125a to 125c may be formed on a position corresponding to one microphone 124, and the microphone 124 may communicate with the outside through the microphone holes 125a to 125c. Meanwhile, the robot 100a may include a plurality of microphones spaced away from each other, and in this case, the robot 100a may sense a direction that the sound is created using the plurality of microphones.

The display 152 may be disposed to face one surface from the robot 100a. Hereinafter, a direction that the display 152 faces defines a front part of the robot 100a. Meanwhile, a speaker 154 is illustrated to be positioned under the robot 100a, but a position of the speaker 154 may be variously changed according to an embodiment.

The light source 156 is implemented with LED and the like, such that a state, an event and the like of the robot 100a may be represented through a change of a color or an output pattern. FIG. 4 illustrates a first light source 156a disposed in both sides of the robots 100a, and a second light source 156b disposed under the robot 100a, but the number and an arrangement position of the light source 156 may be variously changed.

Although not illustrated in the figure, the robot 100a may further include a movement means (a driving means) for moving from one position to the other position. For example, the movement means may include at least one wheel and a motor for rotating the wheel.

Figure 5:
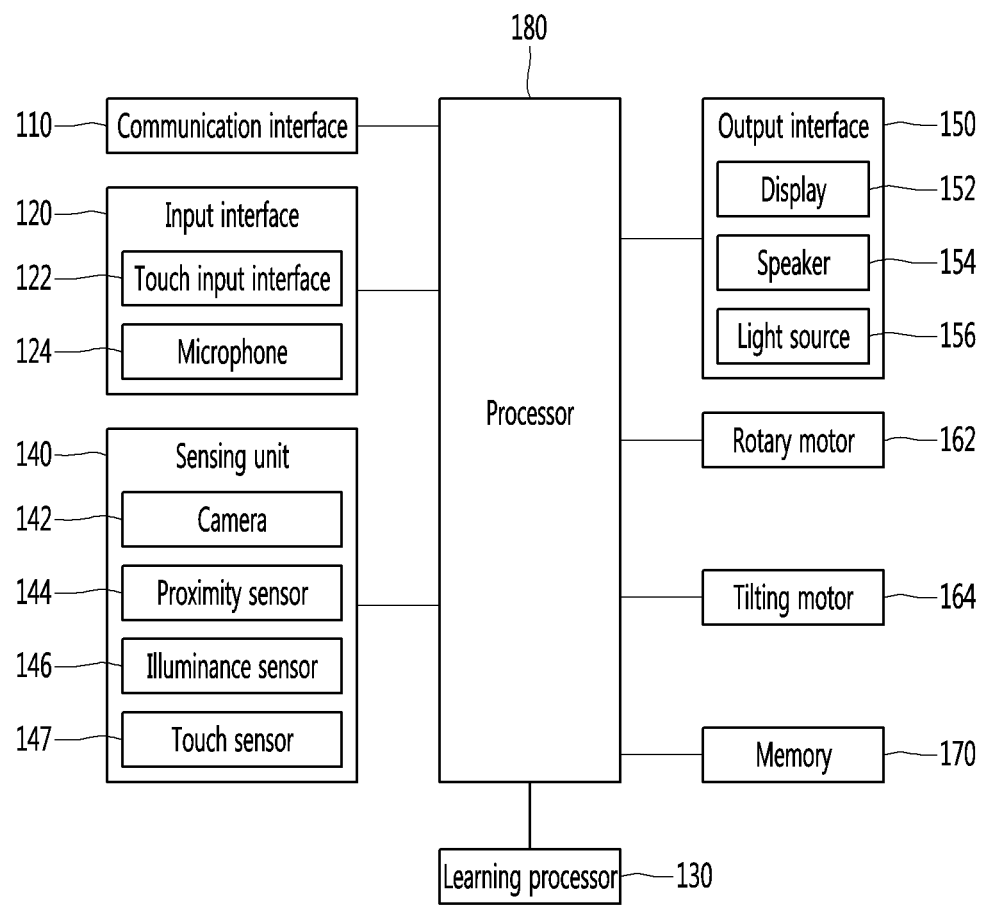
FIG. 5 is a block diagram illustrating a control constitution of the robot according to an embodiment of the present disclosure.

FIG. 5 is a block diagram illustrating a control constitution of the robot according to an embodiment of the present disclosure.

Referring to FIG. 5, the robot 100a may comprise the communication interface 110, the input interface 120, the learning processor 130, the sensing unit 140, the output interface 150, a rotary motor 162, a tilting motor 164, the memory 170 and the processor 180. Constituents illustrated in FIG. 5 are one example for convenience of explanation, and the robot 100a may include more or less constituents than the constituents illustrated in FIG. 5.

Meanwhile, the contents for the AI device 100 of FIG. 1 is similarly applied to the robot 100a of the present disclosure, and thus, the contents overlapping with the contents described in FIG. 1 will be omitted.

The communication interface 110 may include communication modules for connecting the robot 100a to a server, a mobile terminal, another robot and the like, through a network. Each of the communication modules may support one of communication techniques described in FIG. 1.

For example, the robot 100a may be connected to a network through an access point of a router and the like. Accordingly, the robot 100a may provide the server or the mobile terminal with all kinds of information acquired through the input interface 120, the sensing unit 140 or the like, through the network. The information transmitted to the server may be stored in the server, or may be transmitted to the other electronic devices (the mobile terminal, the robot, and the like) connected to the server.

The input interface 120 may include at least one input means for acquiring various kinds of data. For example, the at least input means may include a physical input mean such as a button, a dial or the like, a touch input interface 122 such a touch pad or a touch panel, and the microphone 124 for receiving a sound of the user, a sound around the robot 100a, or the like. According to an embodiment, the touch input interface 122 may be implemented in a touch screen shape with the display 152. The user may input all kinds of requests or commands to the robot 100a through the input interface 120.

Meanwhile, the processor 180 may transmit the user's sound data received through the microphone 124 to the server through the communication interface 110. The server may analyze the sound data to recognize a starting word or a command, a request and the like, in the voice data, and may provide the robot 100a with a recognized result. According to an embodiment, the server may be implemented with the AI server 200 described in FIG. 2, and in this case, the server may recognize the starting word, the command, the request and the like, in the sound data through a model (an artificial neural network 231a) learned through the learning processor 240. The processor 180 may switch an operation mode based the recognized result, or process the command or the request.

According to an embodiment, the processor 180 may directly recognize the starting word, the command, the request and the like, in the sound data, through the model learned by the learning processor 130 in the robot 100a. In addition, the processor 180 may receive data corresponding to the model learned from the server and store the data in the memory 170, and may recognize the starting word, the command, the request and the like, in the sound data through the stored data.

The sensing unit 140 may include at least one sensor for sensing all kinds of information around the robot 100a. For example, the sensing unit 140 may include a variety of sensors such as the camera 142, a proximity sensor 144, an illuminance sensor 146, a touch sensor 147, and the like.

The camera 142 may acquire an image around the robot 100a. According to an embodiment, the processor 180 may recognize the user by acquiring the image including a face of the user through the camera 142, or acquire a gesture, an expression or the like of the user.

The proximity sensor 144 may sense that objects such as the user and the like approach around the robot 100a. For example, when the approach of the user is sensed by the proximity sensor 144, the processor 180 may induce the user to use the robot 100a by outputting an initial screen or an initial voice through the output interface 150.

The illuminance sensor 146 may sense brightness of a space where the robot 100a is arranged. The processor 180 may control constituents so as to perform various operations based on a sensed result and/or time-zone information of the illuminance sensor 146.

The touch sensor 147 may sense that the portion of the user's body contacts a predetermined area of the robot 100a. For example, the touch sensor 147 may preferably, but need not necessarily, be arranged in a head part of the robot 100a, specifically, in an upper part or a rear part of a face area including the display 152.

The output interface 150 may output all kinds of information or contents associated with an operation or a state of the robot 100a, and all kinds of services, programs, applications and the like, executed in the robot 100a. In addition, the output interface 150 may output all kinds of messages or information for performing interaction with the user.

The output interface 150 may include the display 152, the speaker 154, the light source 156, and the like.

The display 152 may output all kinds of information or messages described above, in a graphic shape. According to an embodiment, the display 152 may be implemented in a touch screen shape with the touch input interface 122, and in this case, the display 152 may function not only as an output means but as an input means.

The speaker 154 may output all kinds of information or messages in a voice or audio shape.

The light source 156 may be implemented with LED and the like. The processor 180 may represent the state and the like of the robot 100a through the light source 156. According to an embodiment, the light source 156 is a subsidiary output means, and may provide the user with all kinds of information with the display 152 and/or the speaker 154.

Meanwhile, the robot 100a may include the rotary motor 162 for rotating a head and/or a body based on a vertical axis, and the tilting motor 164 for rotating (tilting) the head and/or the body based on a horizontal axis.

The processor 180 may change a direction that the display 152 and the camera 142 of the robot 100a face, by rotating and/or tilting the robot 100a by controlling the rotary motor 162 and/or the tilting motor 164.

All kinds of data such as control data for controlling operations of constituents included in the robot 100a, data for performing an operation based on an input acquired through the input interface 120 or information acquired through the sensing unit 140, may be stored in the memory 170.

In addition, program data of a software module, an application or the like, executed by at least one processor or controller included in the processor 180, may be stored in the memory 170.

In addition, an interface for representing an emotion expression of the robot 100a through the display 152 may be stored in the memory 170 according to an embodiment of the present disclosure. For example, the interface may include GUI (graphic user interface) outputted through the display 152, and a sound outputted through the speaker 154.

Hardware-wise, such a memory 170 may include a variety of storage devices such as ROM, RAM, EPROM, a flash drive, a hard drive, and the like.

The processor 180 may include at least one processor or controller or the like, for controlling the operation of the robot 100a. Specifically, the processor 180 may include at least one CPU, an AP (application processor), a microcomputer (or a micom), an integrated circuit, ASIC (application specific integrated circuit) and the like.

For example, the processor 180 may include an image signal processor (ISP) for processing an image signal acquired through the camera 142, a display controller for controlling an operation of the display 152, and the like.

Meanwhile, the processor 180 may set a driving mode of the robot 100a to one of various driving modes, based on surrounding environments (e.g., time, illuminance, an input, a user, and a sound and the like), user settings or the like.

Specifically, the driving mode of the robot 100a according to an embodiment of the present disclosure may include a sleep monitoring mode for minimizing sleep interruption while the user is asleep, and minimizing unnecessary power consumption. Referring to the drawings below, embodiments relative to the sleep monitoring mode will be described.

Figure 6:
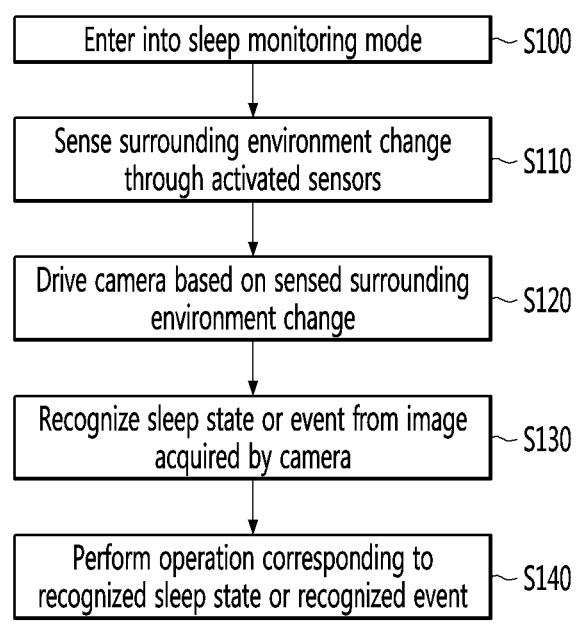
FIG. 6 is a flowchart for explaining a schematic control operation relative to a user monitoring mode of the robot according to an embodiment of the present disclosure.

FIG. 6 is a flowchart for explaining a schematic control operation relative to a user monitoring mode of the robot according to an embodiment of the present disclosure.

The user monitoring mode may correspond to a mode activated in a state that a use frequency of the robot 100a is relatively reduced over a general situation as the user performs specific operations such as sleep, a telephone call, listening to music, a meeting and the like.

According to an embodiment, the user monitoring mode may include at least one monitoring mode according to the state of the user.

For convenience of explanation, in the following drawings, embodiments relative to the sleep monitoring mode is explained as one example of a user monitoring mode, but at least a portion of embodiments relative to the sleep monitoring mode may be applied similarly to other various modes included in the user monitoring mode.

Referring to FIG. 6, the robot 100a can enter into the sleep monitoring mode (S100).

The processor 180 may enter the robot 100a into the sleep monitoring mode, by setting the driving mode of the robot 100a to the sleep monitoring mode in a specific condition.

For example, the processor 180 may set the driving mode to the sleep monitoring mode when a current time approaches a sleep monitoring mode entry time preset or set by the user.

In addition, the processor 180 may set the driving mode to the sleep monitoring mode based on reception of the user's touch input in response to a sleep monitoring mode entry command received through the input interface 120, or a sleep monitoring mode entry command through the touch sensor 147.

In addition, the processor 180 may set the driving mode to the sleep monitoring mode, if illuminance sensed through the illuminance sensor 146 is maintained in a state below a reference illuminance during more than a reference time, or if a state that a sound signal above a predetermined level is not received through the microphone 124 is maintained during more than a predetermined time.

The robot 100a can sense a surrounding environment change of the robot 100a through activated sensors, according to an entry into the sleep monitoring mode (S110).

The processor 180 may inactivate the other constituents except minimum constituents, at a time of entering into the sleep monitoring mode.

For example, the processor 180 may activate only the microphone 124 and/or the illuminance sensor 146, and inactivate the other constituents. In particular, the processor 180 may inactivate driving of constituents such as the camera 142, the display 152 and the like, which have relatively great power consumption.

The use frequency of the robot 100a in the user's sleep may be relatively low over a use frequency in the user's non-sleep. Accordingly, the processor 180 may minimize unnecessary power consumption in the sleep monitoring mode, by inactivating (turning off, etc.) the driving of the constituents such as the camera 142, the display 152, and the like.

Meanwhile, according to an embodiment, the processor 180 may inactivate the driving of the camera 142 and the display 152, after controlling the rotary motor 162 and/or the tiling motor 164 such that the camera 142 and the display 152 face the user, at the time of entering into the sleep monitoring mode. Accordingly, when the camera 142 is activated later, the processor 180 may more rapidly confirm a sleep state of the user from the image acquired through the camera 142.

The processor 180 may sense the surrounding environment change by using the activated sensors (the microphone and the illuminance sensor).

The processor 180 may acquire the sound signal around the robot 100a through the microphone 124, and sense whether a sound corresponding to a predetermined event is included in the acquired sound signal.

In addition, the processor 180 may sense events such as turning on illumination in a space, and the like, by sensing an illumination change around the robot 100a through the illumination sensor 146.

The robot 100a can drive the camera 142 based on the sensed change of the surrounding environment (S120). The robot 100a can recognize the sleep state of the user from the image acquired by the driven camera 142, or recognize an event created around the robot 100a (S130).

Since the sensors (the microphone 124 and the illuminance sensor 146) activated in the sleep monitoring mode senses the change of the surrounding environment from limited sources such a sound, illuminance and the like, the sleep state of the user or sensing accuracy for the event created around the robot 100a may be low over the camera 142.

Therefore, the processor 180 may drive the camera 142 if the change of the surrounding change is sensed through the constituents (the sensors) activated in the sleep monitoring mode.

For example, if an occurrence of a predetermined event is estimated from the sound signal acquired through the microphone 124, the processor 180 may acquire the image around the robot 100a by activating the camera 142, and confirm whether the event occurs based on the acquired event.

In addition, when a rapid change of illuminance is sensed through the illuminance sensor 146 (e.g., turning on lighting), the processor 180 may confirm whether the user is asleep or another person is present, by activating the camera 142.

The robot 100a can perform an operation corresponding to the event or a recognized sleep state (S140).

The processor 180 may sense the sleep state of the user (whether the user is asleep) based on the image acquired through the activated camera 142, or sense the event created around the robot 100a, and may perform a variety of operations based on a sensed result.

Concrete examples relative to operation S130 to operation S140 will be described in detail with reference to FIG. 7 to FIG. 10 below.

Figure 7:
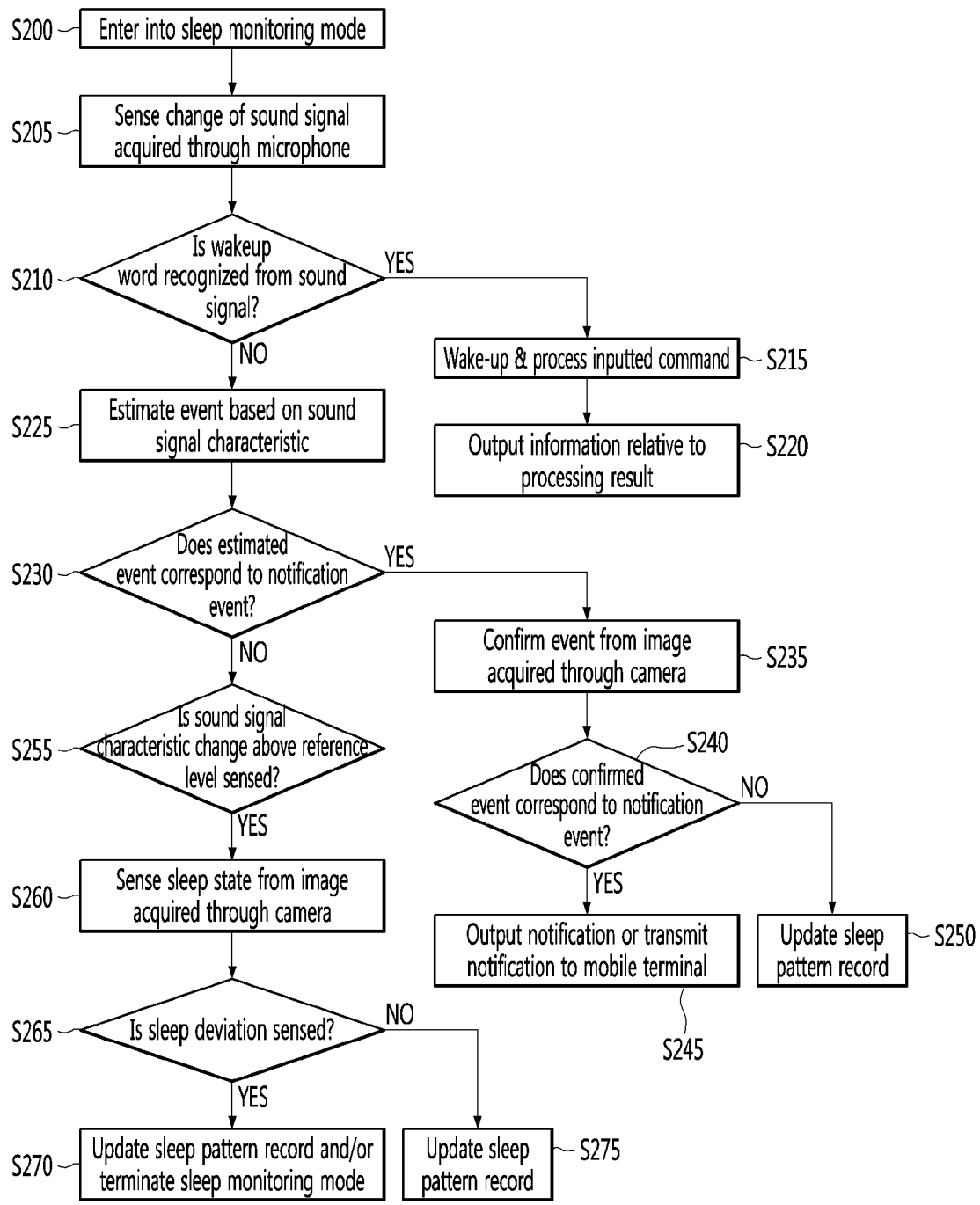
FIG. 7 is a flowchart for explaining an embodiment for a control operation of the robot entering into the sleep monitoring mode.
Figure 8A:
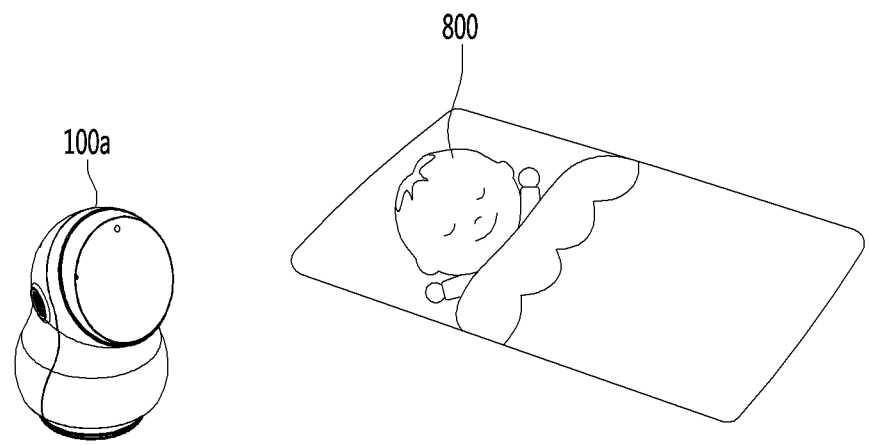
FIGS. 8A to 8D are exemplified views relative to the operation of the robot illustrated in FIG. 7.
Figure 8B:
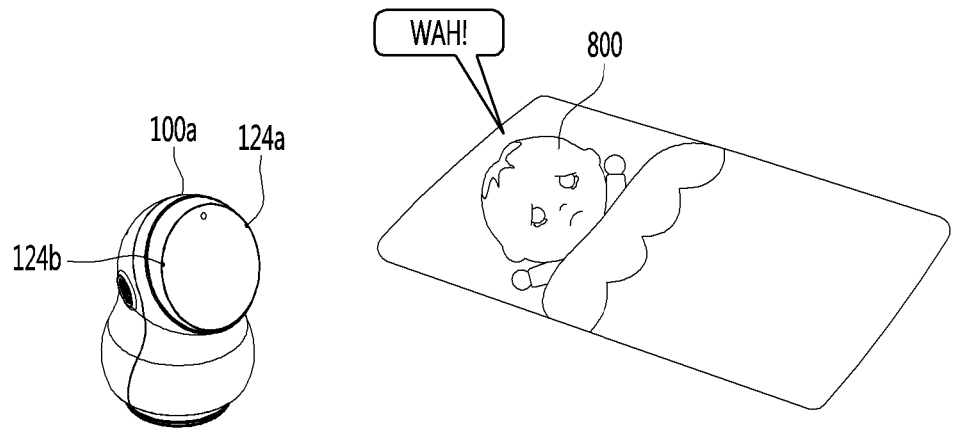
Figure 8C:
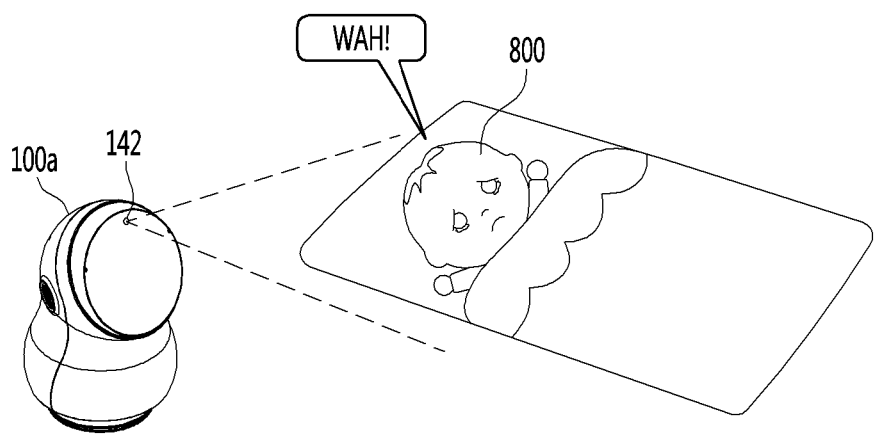
Figure 8D:
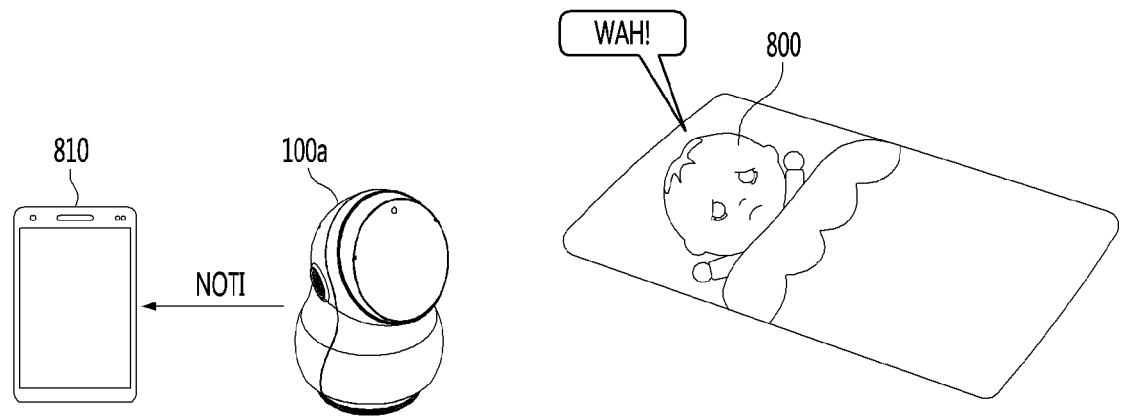
Figure 9A:
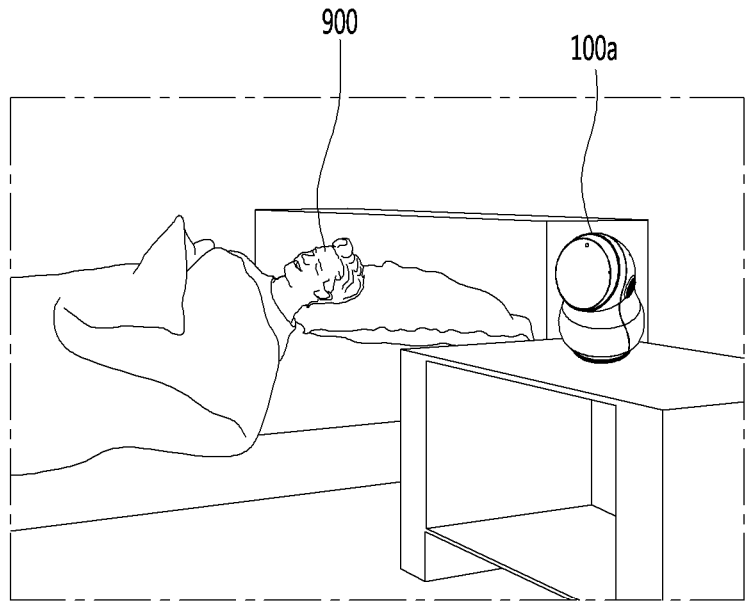
FIGS. 9A and 9B are exemplified views relative to the operation of the robot illustrated in FIG. 7.
Figure 9B:
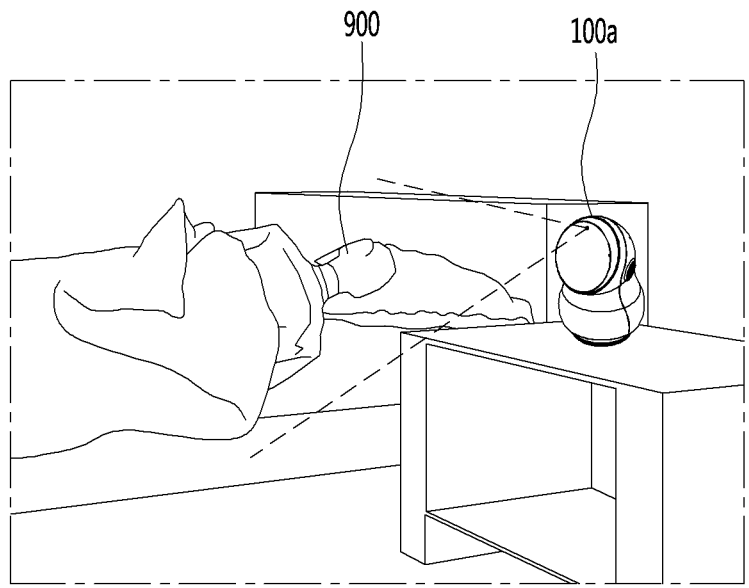

FIG. 7 is a flowchart for explaining an embodiment for a control operation of the robot entering into the sleep monitoring mode. FIGS. 8A to 8D are exemplified views relative to the operation of the robot illustrated in FIG. 7. FIGS. 9A and 9B are exemplified views relative to the operation of the robot illustrated in FIG. 7.

Referring to FIG. 7, the robot 100a can sense a change of the sound signal acquired through the microphone 124 (S205), according to the entry into the sleep monitoring mode (S200).

The processor 180 may continuously acquire the sound signal through the microphone 124, in the sleep monitoring mode.

Meanwhile, when a plurality of microphones are provided in the robot 100a, the processor 180 may reduce the power consumption of the robot 100a by activating only a portion of the plurality of microphones at the time of entering into the sleep monitoring mode. For example, when four microphones are provided in the robot 100a, the processor 180 may activate only two microphones at the time of entering into the sleep monitoring mode.

The processor 180 may sense that the change of the sound signal is created, from the sound signal continuously acquired through the activated microphone 124. For example, the change of the sound signal may be caused by an utterance of the user's wakeup word of and the like, the occurrence of the event around of the robot 100a, and the like.

The robot 100a can confirm whether the change of the sound signal is caused by the utterance of the user's wakeup word, that is, whether the wakeup word is recognized from the sound signal (S210).

The processor 180 may recognize whether a signal characteristic corresponding to the wakeup word previously registered is included in the sound signal of a section that the change occurs.

If the wakeup word is recognized from the sound signal (YES of S210), the processor 180 may wake up the robot 100a, and process a command inputted after the utterance of the wakeup word (S215). The processor 180 can output information relative to a processing result of the command (S220).

As the robot 100a wakes up, the constituents such as the camera 142, the display 152 and the like, which is in an inactivated state, may be activated.

The processor 180 may process the command acquired through the input interface 120, the camera 142 and the like, after the utterance of the wakeup word, and output information relative to the processing result through the output interface 150 of the activated display 152 and the like.

Meanwhile, when the wakeup word is not recognized from the sound signal (NO of S210), the processor 180 can estimate the event based on the signal characteristic of the acquired sound signal (S225).

Signal characteristic information for each of a plurality of events may be stored in the memory 170 of the robot 100a. The signal characteristic information may include information for an intrinsic signal characteristic of a sound relative to the event corresponding to a waveform, a pattern, intensity and the like of the signal. For example, the signal characteristic information may include a sample waveform (a signal) of the sound relative to the event.

The processor 180 may estimate the event corresponding to the sound signal, by comparing the acquired sound signal with a plurality of signal characteristic information stored in the memory 170.

For example, when similarity between first signal characteristic information of a plurality of signal characteristic information and the sound signal is above a reference value, the processor 180 may estimate that an event corresponding to the first signal characteristic information occurs.

When the estimated event corresponds to a notification event (YES of S230), the robot 100a may activate the camera 142, and confirm the event based on the image acquired through the camera 142 (S235).

The notification event may mean an event having an attribute that the user and the like need a notification. For example, the notification event may include events corresponding to emergency situations such as a siren, another person's infringement, child crying and the like. In addition, the notification event may include various events necessary for notification such as a doorbell ring and the like. In addition, the notification event may mean an event to drive the camera 142.

For example, setting information indicating whether each of the plurality of events described above are set to a notification event may be further stored in the memory 170. Based on the setting information stored in the memory 170, the processor 180 may confirm whether the estimated event is set to the notification event.

However, the event estimated based on the sound signal may be different from an event actually occurring. Therefore, the processor 180 may activate the camera 142, in order to more exactly sense the event actually occurring.

The processor 180 may confirm the event from the image acquired through the activated camera 142. For example, based on all kinds of image recognition techniques previously notified, the processor 180 may recognize a state of an object such as a human being and the like in the image, and exactly confirm the event based on a recognized result and the signal characteristic of the sound signal.

When the confirmed event corresponds to the notification event (YES of S240), the processor 180 can output the notification indicating the occurrence of the event through the output interface 150, or can transmit the notification to a mobile terminal capable of communication with the robot 100a (S245).

The processor 180 may activate at least one of the display 152, the speaker 154 or the light source 156 in order to output the notification. That is, the constituents may be inactivated in the sleep monitoring mode, and activated at the time of outputting the notification, thereby using minimum power.

In addition, the processor 180 may control the communication interface 110 to transmit the notification representing the occurrence of the event to the mobile terminal, so as to output the notification through the mobile terminal of the user.

In this regard, referring to FIG. 8A to FIG. 8D, the processor 180 may convert the driving mode of the robot 100a to the sleep monitoring mode, when a monitoring object (e.g., an infant 800) is asleep. As stated above, the processor 180 may drive the rotary motor 162 and/or the tilting motor 164 such that the camera 142 faces the infant 800, at a time of conversion of the sleep monitoring mode.

According to initiation of the sleep monitoring mode, the processor 180 may inactivate the driving of the camera 142 and the display 152. In addition, the processor 180 may activate only portions (a first microphone 124a and a second microphone 124b) of a plurality of microphones.

Meanwhile, the infant 800 may wake up and cry during sleep. In this case, the processor 180 may receive a sound signal including crying of the infant 800 through the activated microphones 124a, 124b.

The processor 180 may estimate the occurrence of the event corresponding to the crying of the infant 800, based on the signal characteristic of the received sound signal. The processor 180 may recognize that the estimated event corresponds to the notification event, based on the information stored in the memory 170.

The processor 180 may activate the driving the camera 142 based on the recognized result. Since the camera 142 is facing the infant 800 at the time of entering into the sleep monitoring mode, the processor 180 may rapidly acquire an image including the infant 800 through the camera 142.

The processor 180 may confirm a state that the infant 800 cries (the occurrence of the event corresponding to the crying), from the acquired image, and may transmit a notification (NOTI) to a mobile terminal 810 of an adult to inform the adult of the confirmed state (event). The adult may take a proper action to the infant 800 by confirming the notification provided through the mobile terminal 810.

Again, FIG. 7 will be described.

On the contrary, if the confirmed event does correspond to the notification event (NO of S240), the processor 180 may update a sleep pattern record of the user based on the confirmed event (S250).

The event estimated based on the sound signal corresponds to the notification event, but the event confirmed using the camera 142 may not correspond to the notification event. For example, if a sound outputted from TV while another person watches TV corresponds to a sound corresponding to the notification event, the event confirmed by the camera 142 does not correspond to the notification event.

In this case, the processor 180 may not perform any separate operation, or may update a sleep pattern record (or a sleep history) of the user based on the kinds (e.g., the user's sleep talking, etc.) of the events confirmed by the camera 142.

Meanwhile, if the event estimated based on the signal characteristic of the sound signal does not correspond to the notification event (NO of S230), the processor 180 may activate the camera 142 based on whether the signal characteristic of the acquired sound signal is changed above a reference level (S255). If at least one of signal characteristics of the sound signal is sensed to be changed above the reference level (YES of S255), the processor 180 may activate the camera 142 and sense the sleep state of the user from the image acquired through the camera 142 (S260).

If the estimate event does not correspond to the notification event, it is not necessary to inform the user of the occurrence of the event, and accordingly, the operation of the camera 142 may not be essential.

In this case, the processor 180 may activate the camera 142 when satisfying a predetermined condition based on the signal characteristics of the sound signal, and may monitor the sleep state of the user from the image acquired through the activated camera 142 or monitor a situation around the robot 100*a*.

The signal characteristic may include a volume, a frequency, a duration time and the like of the signal. That is, the processor 180 may activate the camera 142 if the volume of the acquired sound signal is changed above a reference volume, if a frequency change degree of the sound signal is above a reference level, and/or if the duration time of a predetermined sound included in the sound signal is above the reference time.

For example, the processor 180 may activate the camera 142 if the duration time is above a first reference time after the sound signal included in the predetermined sound is created. Meanwhile, according to an embodiment, the processor 180 may not activate the camera 142 if the during time of the sound signal is above a second reference time longer than the first reference time (e.g., a sound created because another person watches TV).

If the user deviates from sleep, that is, the user is sensed not to be asleep (YES of S265), the processor 180 can update the sleep pattern record of the user, and terminal the sleep monitoring mode (S270).

The processor 180 may monitor the sleep state of the user, by using the image included in a sleep position of the user.

The processor 180 may recognize that the user wakes up at the time of creating the sound signal, if the user is not included in the image, the user is spaced apart above a predetermined distance from the sleep position, or if a posture of the user is sensed not to be asleep, e.g., a sitting position, a standing position or the like. According to an embodiment, if the user is not included in the image, the processor 180 may acquire the image by changing a direction that the camera 142 faces by controlling the rotary motor 162 and/or the tilting motor 164, in order to confirm the position of the user.

Accordingly, the processor 180 may update the sleep pattern record with the user waking up at the time of creating the sound signal or at the time of acquiring the image. In addition, the processor 180 may terminal the sleep monitoring mode. That is, the processor 180 may easily acquire information for a wake-up time without a separate input of the user.

On the contrary, if the user is sensed to be asleep (NO of S265), the processor 180 may update the sleep pattern record of the user based on a sensed result (S275).

If the user is sensed to be asleep from the acquired image, the processor 180 may maintain the sleep monitoring mode. In addition, the processor 180 may update the sleep pattern record (the sleep history) based on whether to make a movement of the user in sleep, and/or based on kinds of sounds created from the user.

For example, if the sound signal including a sound corresponding to snoring is acquired through the microphone 124 and the user is sensed to be asleep from the image acquired through the camera 142, the processor 180 may update the sleep pattern record of the user with occurrence of the snoring at the time of occurrence of the sound signal or at the time of acquiring the image.

In addition, if the user is sensed to twist and turn in sleep from the image acquired through the camera 142, the processor 180 may update the sleep pattern record of the user with occurrence of the user's twisting and turning at the time of creating the sound signal or at the time of acquiring the image.

In this regard, referring to FIGS. 9A and 9B, the processor 180 may convert the driving mode of the robot 100*a* into the sleep monitoring mode, when a monitoring object (e.g., a user 900) is asleep. As stated above, the processor 180 may drive the rotary motor 162 and/or the tilting motor 164 such that the camera 142 faces the user 900, at the time of conversion of the sleep monitoring mode.

According to initiation of the sleep monitoring mode, the processor 180 may inactivate the driving of the camera 142 and the display 152. In addition, the processor 180 may activate only portions (a first microphone 124*a* and a second microphone 124*b*) of a plurality of microphones.

Meanwhile, the user 900 may change a sleep posture (twisting and turning) in sleep, and the processor 180 may receive the sound signal including the sound created when the user 900 twists and turns through the activated microphones 124*a* and 124*b*.

The processor 180 may estimate the occurrence of the event corresponding to the twisting and turning of the user 900 based on the signal characteristic of the received sound signal. The processor 180 may recognize that the estimated event does not correspond to the notification event, based on the information stored in the memory 170.

In this regard, the processor 180 may activate the driving of the camera 142, when during time of the sound signal is sensed to be above a reference time. Since the camera 142 is facing the user 900 at a time of entering into the user monitoring mode, the processor 180 may rapidly acquire the image including the user 900 through the camera 142.

The processor 180 may confirm that the user 900 twists and turns, if a movement corresponding to the twisting and turning of the user 900 is sensed from the acquired image, or a sleep posture of the user 900 is sensed to differ from the sleep posture of the image previously acquired. The processor 180 update the sleep pattern record SLEEP_RECORD such that the occurrence of the twisting and turning of the user 900 is displayed at the time of creating the sound signal or at the time of acquiring the image.

Although not illustrated in the figure, if the twisting and turning of the user 900 is sensed to be terminated, the processor 180 may inactivate the camera 142 again.

That is, according to embodiments illustrated in FIGS. 7 to 9B, the robot 100a may activate the microphone 124 having relatively low power consumption to perform the monitoring operation, at the time of conversion of the sleep monitoring mode, and may minimize consumption of standby power by inactivating the driving of the camera 142, and the display 152 and the like, which have relatively high power consumption.

In addition, since the robot 100a performs an operation only if a specific event is confirmed through the microphone 124 and the camera 142, the user's sleep interruption caused by frequent driving or wake-up in the user's sleep may be minimized.

In addition, the robot 100a may effectively provide information relative to the sleep such as the user's sleep habit and the like, by recording the sleep history of the user based on the event sensed during driving in the sleep monitoring mode.

FIG. 10 is a flowchart for explaining an embodiment for a control operation of the robot entering into the sleep monitoring mode.

For convenience of explanation, the present specification divides and describes embodiments into embodiments of FIG. 7 and FIG. 10, respectively, but the embodiment of FIG. 7 and the embodiment of FIG. 10 may be applied in parallel to the robot 100a. That is, the robot 100a may perform an operation according to the embodiment of FIG. 7 and an operation according to the embodiment of FIG. 10 together, by activating the microphone 124 and the illuminance sensor 146 at the time of entering into the sleep monitoring mode.

Referring to FIG. 10, the robot 100a can sense illuminance of a space where the robot 100a is arranged through the illuminance sensor 146 (S310), according to an entry into the sleep monitoring mode (S300).

Similar to what is described in FIG. 6, the processor 180 may inactivate the constituents such as the camera 142, the display 152 and the like, and activate the illuminance sensor 146 at the time of entering into the sleep monitoring mode.

The processor 180 may sense the illuminance of the space periodically or continuously through the illuminance sensor 146.

For example, the sensed illuminance is below a preset reference illuminance, while the user is asleep. In addition, the sensed illuminance may be maintained below the reference illuminance, in a state that lighting of the space where the robot 100a is arranged is turned off, or in a state that any other light such as light of the sun and the like is not irradiated from the outside.

If a change of the illuminance is sensed (YES of S320), the robot 100a may sense the sleep state of the user from the image acquired through the camera 142 (S330).

For example, the processor 180 may activate the driving of the camera 142, if the illuminance sensed through the illuminance sensor 146 is above the reference illuminance.

According to an embodiment, the processor 180 may activate the driving of the camera 142, if a difference between previously sensed illuminance and currently sensed illuminance is above a reference value (e.g., lighting being on).

The processor 180 may sense the sleep state of the user from the image acquired through the activated camera 142.

If the user deviates from sleep, that is, the user is sensed to wake up (YES of S340), the robot 100a can update the sleep pattern record of the user, and/or perform termination of the sleep monitoring mode (S350).

As described above, the processor 180 may recognize that the user wakes up, if the user is not included in the image acquired from the camera 142, the user is recognized, from the image, to be spaced apart above a predetermined distance from the sleep position, or a sitting position or a standing position of the user is recognized.

If the user is recognized to wake up, the processor 180 may update the sleep pattern record by estimating a sensing time of an illuminance change or an acquiring time of the image to a wake-up time of the user. In addition, the processor 180 may terminal the sleep monitoring mode. Accordingly, the processor 180 may acquire information relative to the wake-up time without a separate input of the user.

Although now illustrated in the figure, the processor 180 may reconvert the driving mode of the robot 100a into the sleep monitoring mode, if the illuminance sensed through the illuminance sensor 146 after terminating the sleep monitoring mode is low below reference illuminance, and the user is sensed to re-enter into the sleep state from the image acquired through the camera 142.

In contrast, if the user is sensed to be asleep (NO of S340), the robot 100a may maintain the sleep monitoring mode or induce the user to wake up, based on existence of another person or a current time (S360).

A case that the user is sensed to be still asleep though illuminance sensed by the illuminance sensor 146 is above the reference illuminance may correspond to a case that another person turns on lighting, a case that the light of the sun is irradiated due to passing of a sunrise time, and the like.

That is, the processor 180 may recognize that the lighting is turned on by another person, if the user is sensed to be asleep, and another person's existence adjacent to an illuminance switch or another person's movement is sensed in the image acquired from the camera 142. In this case, the processor 180 may maintain the sleep monitoring mode.

In addition, the processor 180 may induce the user to wake up, if the current time is after the sunrise time, the current time is within a predetermined time from a scheduled time for the user to wake up, or the current time passes the scheduled time to wake up. For example, the processor 180 may output a sound of inducing the user to wake up through the speaker 154.

According to an embodiment of FIG. 10, the robot 100a may minimize the sleep interruption due to the driving of the robot 100a while the user is asleep, and minimize the power consumption of the robot 100a, by providing the sleep monitoring mode of driving the camera 142 and the like based on a peripheral illuminance.

In addition, the robot 100a may provide effectively information of the sleep habit and the like of the user, by recording the sleep history of the user through the sleep monitoring mode.

According to an embodiment, the robot may activate only minimum constituents such as the microphone and/or the illuminance sensor and the like in a state that a use frequency of the robot is relatively reduced over general states such as the user falling asleep and the like, and provide the user monitoring mode of monitoring the user's situation or a surrounding situation, thereby minimizing the power consumption of the robot.

In addition, if a result sensed through the microphone and/or the illuminance sensor satisfies a specific condition, the robot may drive the constituents such as the camera and the like, and perform a predetermined operation, thereby minimizing interruption for the user according to frequent driving or a wake-up of the user.

In addition, the robot may record a history relative to the user's state based on all kinds of information sensed during driving in the user monitoring mode, thereby effectively providing all kinds of useful data such as the user's sleep habit and the like.

The foregoing description is merely illustrative of the technical idea of the present disclosure, and various changes and modifications may be made by those skilled in the art without departing from the essential characteristics of the present disclosure.

Therefore, the embodiments disclosed in the present disclosure are to be construed as illustrative and not restrictive, and the scope of the technical idea of the present disclosure is not limited by these embodiments.

The scope of the present disclosure should be construed according to the following claims, and all technical ideas within equivalency range of the appended claims should be construed as being included in the scope of the present disclosure.

What is claimed is:

1. A robot comprising:
    a microphone;
    a camera disposed to face a predetermined direction; and
    a processor configured to:
        inactivate driving of the camera and activate driving of the microphone, if a driving mode of the robot is set to a user monitoring mode;
        acquire a sound signal through the microphone;
        activate the driving of the camera based on an event estimated from the acquired sound signal;
        confirm the event from the image acquired through the camera; and
        control at least one constituent included in the robot to perform an operation based on the confirmed event,
    wherein the user monitoring mode includes a sleep monitoring mode set when the user is asleep, and the processor is configured to:
        activate the driving of the camera according to a signal characteristic of the acquired sound signal if the estimated event does not correspond to a notification event;
        sense a sleep state of the user from the image acquired through the activated camera; and
        update a sleep history of the user based on the sensed sleep state or terminate the sleep monitoring mode.

2. The robot of claim 1, wherein the processor is configured to:
    estimate the event based on the signal characteristic of the acquired sound signal; and
    activate the driving of the camera, if the estimated event corresponds to the notification event.

3. The robot of claim 2, further comprising a memory configured to store signal characteristic information of each of a plurality of events and setting information relative to whether to set the notification event for each of the plurality of events,
    wherein the processor is configured to:
        estimate the event based on a comparison result by comparing a plurality of signal characteristic information stored in the memory and a signal characteristic of the acquired sound signal; and
        confirm whether the estimated event from the setting information corresponding to the estimated event corresponds to the notification event.

4. The robot of claim 3, further comprising an output interface including at least one of a display, a speaker or a light source,
    wherein the processor is configured to activate the output interface to output a notification associated with the confirmed event, if an event confirmed from the image acquired through the activated camera corresponds to the notification event.

5. The robot of claim 3, further comprising a communication interface for a communication connection with a mobile terminal,
    wherein the processor is configured to control the communication interface to transmit the notification associated with the confirmed event to the mobile terminal, if the event confirmed from the image acquired through the activated camera corresponds to the notification event.

6. The robot of claim 3, wherein the processor is configured to update a history associated with a current state of a user based on the confirmed event, if the event confirmed from the image acquired through the activated camera does not correspond to the notification event.

7. The robot of claim 2, wherein the processor is configured to activate the driving of the camera according to the signal characteristic of the acquired sound signal, if the estimated event does not correspond to the notification event, and
    the signal characteristic includes at least one of a volume of the sound signal, a duration time or a frequency change degree.

8. The robot of claim 1, wherein the processor is configured to update the sleep history with the user waking up at a time of creating the sound signal or at a time of acquiring the image and terminate the sleep monitoring mode, if the user is sensed not to be asleep.

9. The robot of claim 1, wherein the processor is configured to:
    maintain the sleep monitoring mode, if the user is sensed to be asleep; and
    update the sleep history based on whether to make a movement of the user acquired from the image, or based on kinds of sounds created from the user recognized through the sound signal.

10. The robot of claim 1, further comprising an output interface including at least one of a display, a speaker or a light source,
    wherein the processor is configured to:
        activate the output interface, if a wakeup word is recognized from the acquired sound signal; and
        output information associated a processing result of a command inputted after uttering the wakeup word, through the output interface.

11. The robot of claim 1, further comprising at least one motor for changing a direction that the camera faces,
   wherein the processor is configured to control the at least one motor such that the camera faces a position including the user, if the driving mode is set to the user monitoring mode.

12. The robot of claim 1, wherein the user monitoring mode include a sleep monitoring mode driven when the user is asleep, and
   the processor is configured to set the driving mode of the robot to the sleep monitoring mode, if a current time reaches a time of entering into the sleep monitoring mode, if a sound signal including a sound above a predetermined volume through the microphone is not received during more than a reference time, or if illuminance sensed through an illuminance sensor is maintained in a state below a reference illuminance during more than a reference time.

13. The robot of claim 12, wherein the processor is configured to:
   activate driving of the illuminance sensor, if the driving mode of the robot is set to the sleep monitoring mode;
   activate the driving of the camera based on the illuminance sensed through the illuminance sensor; and
   confirm whether the user is asleep from the image acquired through the activated camera.

14. The robot of claim 13, wherein the processor is configured to update a sleep history with the user waking up at a time of sensing the illuminance sensor or at a time of acquiring the image and terminate the sleep monitoring mode, if the user is sensed not to be asleep.

15. A method for controlling the robot, comprising:
   inactivating driving of a camera and activating driving of a microphone, according to an entry of a user monitoring mode;
   receiving a sound signal through the microphone;
   activating the driving of the camera based on an event estimated from the received sound signal;
   confirming the event from an image acquired through the activated camera; and
   controlling at least one constituent included in the robot to perform a processing operation based on the confirmed event,
   wherein the user monitoring mode includes a sleep monitoring mode driven when the user is asleep, and controlling the at least one constituent includes:
      sensing a sleep state of the user from the image acquired through the activated camera; and
      updating a sleep history of the user based on the sensed sleep state or terminating the sleep monitoring mode.

16. The method of claim 15, wherein when the confirmed event is set to a notification event, the controlling the at least constituent comprises at least one of:
   activating an output interface included in the robot to output a notification associated with the confirmed event; or
   controlling a communication interface to transmit the notification to a mobile terminal,
   wherein the output interface comprises at least one of a display, a speaker or a light source.

17. The method of claim 15, wherein when the confirmed event is not set to a notification event, the controlling the at least constituent comprises:
   estimating the event based on a signal characteristic of the received sound signal; and
   activating the driving of the camera according to a signal characteristic of the received sound signal, if the estimated event does not correspond to the notification event, and
   the signal characteristic includes at least one of a volume of the sound signal, a duration time or a frequency change degree.

18. The method of claim 17, wherein the user monitoring mode comprises a sleep monitoring mode driven when the user is asleep, and the updating the history comprises:
   updating a sleep history with the user waking up at a time of creating the sound signal or at a time of acquiring the image, if the user is sensed not to be asleep; and
   updating the sleep history based on whether to make a movement of the user, or based on kinds of sounds recognized through the sound signal, if the user is asleep.

19. The method of claim 15, further comprising controlling at least one motor included in the robot such that the camera faces a position including the user, at a time of entering into the user monitoring mode.

20. A robot comprising:
   a microphone;
   a camera disposed to face a predetermined direction; and
   a processor configured to:
      inactivate driving of the camera and activate driving of the microphone, if a driving mode of the robot is set to a user monitoring mode;
      acquire a sound signal through the microphone;
      activate the driving of the camera based on an event estimated from the acquired sound signal;
      confirm the event from the image acquired through the camera; and
      control at least one constituent included in the robot to perform an operation based on the confirmed event,
   wherein
      the user monitoring mode include a sleep monitoring mode driven when the user is asleep, and
      the processor is configured to set the driving mode of the robot to the sleep monitoring mode, if a current time reaches a time of entering into the sleep monitoring mode, if a sound signal including a sound above a predetermined volume through the microphone is not received during more than a reference time, or if illuminance sensed through an illuminance sensor is maintained in a state below a reference illuminance during more than a reference time.

* * * * *